US011284790B2

United States Patent
Gomez et al.

(10) Patent No.: US 11,284,790 B2
(45) Date of Patent: *Mar. 29, 2022

(54) LAPAROSCOPIC VISUALIZATION SYSTEM

(71) Applicant: Covidien LP, Mansfield, MA (US)

(72) Inventors: Ricardo Alexander Gomez, Lighthouse Point, FL (US); Sandy Lawrence Heck, Los Angeles, CA (US); Eric William Conley, South Berwick, ME (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/830,862

(22) Filed: Mar. 26, 2020

(65) Prior Publication Data

US 2020/0288957 A1    Sep. 17, 2020

Related U.S. Application Data

(63) Continuation of application No. 15/384,855, filed on Dec. 20, 2016, now Pat. No. 10,617,289, which is a
(Continued)

(51) Int. Cl.
*A61B 1/00* (2006.01)
*A61B 90/70* (2016.01)
(Continued)

(52) U.S. Cl.
CPC .......... *A61B 1/128* (2013.01); *A61B 1/00032* (2013.01); *A61B 1/00055* (2013.01);
(Continued)

(58) Field of Classification Search
CPC ......... A61B 1/127; A61B 1/123; A61B 1/128; A61B 1/126; A61B 1/121; A61B 1/00131;
(Continued)

(56) References Cited

U.S. PATENT DOCUMENTS 3,735,310 A * 5/1973 Kochanski ........... H01H 61/013
337/107
3,738,174 A * 6/1973 Waldron .............. G01K 15/005
374/173
(Continued)

*Primary Examiner* — John P Leubecker
(74) *Attorney, Agent, or Firm* — McCormick, Paulding & Huber PLLC

(57) ABSTRACT

A Laparoscopic Visualization System comprising a sterile, self-contained, disposable apparatus used in medical procedures for heating and applying an anti-fog solution to the distal end of laparoscopes or surgical devices is presented. It additionally serves as an endoscopic lens protector and cleaner. An efficient heating and narrow range temperature control mechanism is used in combination with an anti-fog solution to provide clear visualization through a distal lens of the surgical device inserted into the system. The configuration prevents the anti-fog solution from spilling out of the system and is designed to also be used as a holder for the surgical scope, protecting the distal lens from impact with a shock absorbent outer shell, prior to, during, and after a medical procedure.

20 Claims, 11 Drawing Sheets

Related U.S. Application Data continuation of application No. 14/102,796, filed on Dec. 11, 2013, now Pat. No. 9,526,409.

(60) Provisional application No. 61/879,668, filed on Sep. 18, 2013.

(51) Int. Cl.
*A61B 1/12* (2006.01)
*A61B 1/313* (2006.01)
*A61B 50/00* (2016.01)

(52) U.S. Cl.
CPC ...... *A61B 1/00068* (2013.01); *A61B 1/00103* (2013.01); *A61B 1/00131* (2013.01); *A61B 1/123* (2013.01); *A61B 1/126* (2013.01); *A61B 1/127* (2013.01); *A61B 1/3132* (2013.01); *A61B 2050/0016* (2016.02); *A61B 2090/701* (2016.02)

(58) Field of Classification Search
CPC .... A61B 2050/0016; A61B 2050/0018; A61B 2090/701
See application file for complete search history.

(56) References Cited

U.S. PATENT DOCUMENTS

| | | | | |
|---|---|---|---|---|
| 3,886,739 A * | 6/1975 | Lee | ............. | F01N 3/2842 60/286 |
| 3,972,681 A * | 8/1976 | Clack | ............. | G01N 25/4893 422/51 |
| 4,112,734 A * | 9/1978 | Goryachev | ............. | G01K 17/00 374/11 |
| 4,831,241 A * | 5/1989 | Shikama | ............. | H05B 3/14 219/504 |
| 4,911,057 A * | 3/1990 | Fishman | ............. | G10D 3/04 84/731 |
| 4,946,082 A * | 8/1990 | Brun | ............. | B22D 41/50 222/593 |
| 5,162,977 A * | 11/1992 | Paurus | ............. | H05K 1/162 174/68.1 |
| 5,880,779 A * | 3/1999 | Rhynes | ............. | H04N 9/735 348/223.1 |
| 6,021,303 A * | 2/2000 | Terada | ............. | G03G 15/2053 399/328 |
| 6,089,146 A * | 7/2000 | Nam | ............. | A23L 3/003 99/468 |
| 6,140,614 A * | 10/2000 | Padamsee | ............. | A47J 36/2466 219/438 |
| 2002/0195442 A1* | 12/2002 | Lee | ............. | H05B 1/0272 219/505 |
| 2004/0173457 A1* | 9/2004 | Miller | ............. | G05D 23/1931 204/451 |
| 2004/0203175 A1* | 10/2004 | Li | ............. | G01N 30/84 436/180 |
| 2007/0000908 A1* | 1/2007 | Bohan, Jr. | ............. | F24F 11/30 219/505 |
| 2008/0099000 A1* | 5/2008 | Suzuki | ............. | F02B 25/00 123/574 |
| 2008/0161646 A1* | 7/2008 | Gomez | ............. | A61B 1/2676 600/169 |
| 2010/0089901 A1* | 4/2010 | Montana | ............. | A47J 36/2466 219/385 |
| 2011/0290773 A1* | 12/2011 | Wu | ............. | H05B 3/58 219/201 |
| 2012/0187104 A1* | 7/2012 | Heymann | ............. | A61B 1/00144 219/385 |
| 2013/0035751 A1* | 2/2013 | Shalev | ............. | A61B 5/01 623/1.12 |
| 2014/0197158 A1* | 7/2014 | Ijuin | ............. | G07F 17/0078 219/628 |

\* cited by examiner

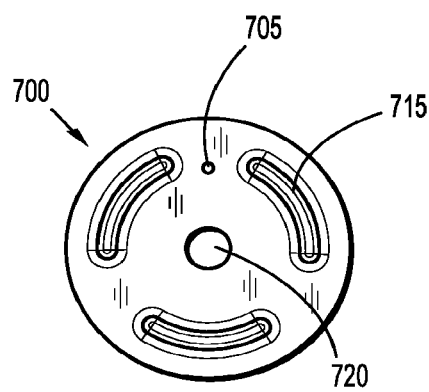
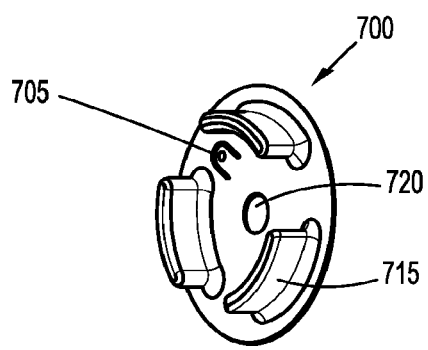
FIG. 7A    FIG. 7B
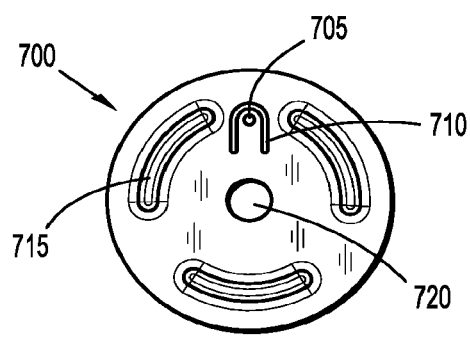
FIG. 7C

LAPAROSCOPIC VISUALIZATION SYSTEM

CROSS REFERENCE TO RELATED APPLICATION

This application is a continuation of U.S. patent application Ser. No. 15/384,855, filed Dec. 20, 2016, which is continuation of prior U.S. patent application Ser. No. 14/102,796, filed on Dec. 11, 2013, which claims the benefit of U.S. Provisional Patent Application Ser. No. 61/879,668 filed on Sep. 18, 2013, which are hereby incorporated by reference in their entirety.

FIELD OF INVENTION

The current invention is directed to the field of Laparoscopic devices, particularly to a Laparoscopic Visualization System, used in minimally invasive surgery and other medical procedures. More particularly, the present invention relates to a significantly improved sterile, compact, disposable apparatus used for heating, applying anti-fog solution to, and protecting of the surgical scope distal lens prior to and during a surgical procedure.

BACKGROUND OF INVENTION

This invention generally relates to a device and system for heating sterile liquid solutions prior to and during medical procedures for producing optimum Laparoscopic visualization.

Laparoscopic surgery sometimes called keyhole or "Minimally Invasive Surgery" (MIS), is a relatively new type of surgery that involves the introduction of small incisions in a patient, (usually between 0.5 and 1.5 cm) whereby access to the thoracic, abdominal or pelvic cavities is obtained by the use of a medical device called a trocar.

Prior to starting a surgical procedure a small incision is performed on the patient whereby a trocar is inserted around the periphery of the incision. The trocar is then replaced with a cannula, device that allows insertion of medical devices. An insufflator also referred to as a pump, is used to inflate the cavity area with carbon dioxide thus providing a means of viewing and creating space for the surgeon to perform the medical procedure. A special medical device called a laparoscope is subsequently inserted through the cannula whereby the surgeon initially looks inside the cavity area in question and determines the best approach for performing the medical procedure.

The invention of high resolution image processing devices has revolutionized laparoscopic surgery. When laparoscopic surgery is performed surgeons have the option of using either a telescopic rod lens system (TRLS) which is a rigid device connected to a high resolution image processing device or a digital laparoscope which uses a charge coupled device. A charged couple device or CCD is often used in image processing devices. Its advantage is that it is small, and compact. It captures images based on the strength of the electric charge received from an image. The stronger the source of received light, the stronger the electric charge created. This electronic information is then transferred electrically to a processing device that converts the received signal to a pixel intensity, thus creating a smooth image screen. The advantage in using this system is that it is very small and flexible thus providing maneuvering room for the surgeon to look into small, difficult to reach areas.

Prior to the invention of Laparoscopic surgery, patients were subject to major invasive procedures, which increased pain, scaring, hemorrhaging, trauma, complications and long recovery times. Through the use of small incisions most of these setbacks have been minimized. The modern use of imaging devices has opened up a window for surgeons to safely view the inside cavities of a person and perform many types of surgeries.

The biggest problem surgeons face with Laparoscopic procedures is being able to see clearly once they are inside a cavity, such as the abdomen of their patient. Clouding is a problem that occurs, caused by contact of the distal lens with body fluids, burnt tissue and other debris, making it difficult for the surgeon to see clearly.

Therein lies the problem. Thus there exists in the industry a need for a Laparoscopic Visualization System that is easy to use, and provides exceptional clarity. There are bulky devices in the industry for cleaning the lenses of Laparoscopes but they are not practical. Some surgeons have been known to place their Laparoscopes into a warm bucket of distilled water and dunk it every time cleaning is needed. In some countries this procedure has been banned. The present invention overcomes these problems by providing a Laparoscopic Visualization System that is efficient and well suited for quick and dependable usage.

SUMMARY OF INVENTION

The following patents are incorporated in their entirety by reference: U.S. Pat. No. 7,080,641 B2, a Method and Apparatus for Heating Sterile Solutions during Medical Procedures, U.S. Pat. No. 7,311,660 B2, a Method and apparatus for Heating and Applying Warm Anti-fog Solution to Endoscopes As Well As Distal Lens Protector, U.S. Pat. No. 7,803,109 B2, Method and Apparatus for Protecting Distal Lens of Endoscopes, and U.S. Pat. No. 8,152,717 B2, a Device for White Balancing and Applying An Antifog Agent to Medical Videoscopes prior to Medical Procedures.

The current application is directed toward a Laparoscopic Visualization System used in the cleaning of lenses of Laparoscopes/Endoscopes by applying a warm anti-fog solution to the distal lens of the device. The anti-fog solution is quickly and efficiently heated and maintained at body temperature to minimize fogging. The system also protects the distal lens. The Laparoscopic Visualization System also has the additional function of providing a means of white balancing.

Significant improvements have been made to the following elements of the Laparoscopic Visualization System. Among them are: a significantly improved heating element or coil, an ergonomic inner frame, an improved thermoswitch which maintains a more stable temperature within the device, an improved power source, a more efficient heating circuit, an efficient low consumption indicator, an efficient printed circuit board, an efficient can assembly, a specialized reducer and an improved valve assembly. These significant changes have dramatically reduced human error and significantly improved control and efficiency of the device.

The present invention discloses an apparatus that combines the benefits of both heat and anti-fog solution, providing superior anti-fogging during the entire surgical procedure. The apparatus is compact and designed to be placed over the distal lens prior to and during a medical procedure. By allowing the lens to bathe in the warm anti-fogging solution, as opposed to just wiping it in the solution, the effectiveness of the anti-fogging solution is greatly increased. The apparatus includes a solid foam outer shell with an interior divided into several compartments. A reservoir in the center of the apparatus is filled with an anti-fog solution of a surfactant in water. The Laparoscopic Visualization System is found useful when a distal end of a surgical instrument is inserted through a self-sealing valve of the system, and is submerged within the anti-fog solution within the receptacle. The instrument is simultaneously heated and bathed in the warm surfactant solution in water. The hard frame and soft interior of the can assembly create a protective barrier around the delicate instrument's distal end. When not in use, the scope can rest inside the Laparoscopic Visualization System, protecting the scope from damage potentially caused by other instruments and trays. Protecting the scope is a very beneficial attribute since scopes are very expensive and are frequently scratched or damaged during procedures, costing hospitals a great deal of money. By heating the solution and the instrument, the significant temperature difference between the interior of the body (98.6.degree. F.) and the room temperature of the instrument are eliminated. This temperature normalization inhibits the condensation of moisture, which occurs upon inserting the cool scope into a warm body cavity. By combining heat with the use of an anti-fogging solution, fogging is prevented from occurring at insertion and during cauterization procedures when smoke and heat are generated within the body cavity.

The main power source may be either an internal or external type. A sterile self-contained battery source is the preferred embodiment. In the preferred embodiment a power supply consisting of three (3) AA batteries, are used and secured into a battery pack. Among the advantages of using batteries are their cost effectiveness and efficiency. By removing the bottom cover and pulling out the battery pack, the batteries can be disposed of in a safe and environmentally friendly manner. The advantage of using an internal battery configuration is that it provides a self-contained sterile environment facilitating its introduction into the operating room. Any typical battery can be used such as NiCad, Lithium, and Alkaline. In another embodiment an external AC (plugged) power source may be used. Among its advantages is that it is cost effective for maintenance over longer periods of time. In the ideal embodiment, the battery source should last as long as the surgery, a minimum of 1 hour and in the preferred embodiment, 4-6 hours. The battery configuration is easier for the user to employ, because the batteries are pre-installed and already in a sterile environment. As a means of holding the batteries together they can be spot welded together or into a battery holder. The advantage of spot welding is that it provides a means of securely holding the batteries together and making the connections more stable and permanent; the disadvantage is that it increases manufacturing time. In another embodiment custom batteries can also be used. Once the procedure is completed the Laparoscopic Visualization System can be safely disposed of. The batteries may also be pulled out from the bottom and properly disposed of.

In the present invention basic circuitry, there is a power source connected to an On/Off switch. The On/Off switch is connected in series with a parallel circuit consisting of a first path having a heating coil in series with a thermoswitch and a secondary path consisting of a resistor in series with a light emitting diode (LED). The integrated circuitry is located on a printed circuit board (PCB). The components can also be individually assembled and connected without the use of a PCB. The PCB is part of the mechanical assembly used to form the Laparoscopic Visualization System shape. The main advantage of the printed circuit board is its reduced wiring and compact circuitry. This circuitry design has been found to be the most effective for the present invention. This simplified construction reduces human error and failure by compartmentalizing individual parts into pre-assembled sub-assemblies.

A blue LED is used for indication. The wavelength of the blue LED is in the range of 400 nm which is among the most energetic. Since an LED produces light in a narrow band of wavelengths phosphors are sometimes used to improve the spectrum of the light produced. It is also possible to combine several different LEDs, each producing a different wavelength to indicate different stages of the battery cycle such as when the level of power is decreasing.

The Laparoscopic Visualization System provides optimum visualization during laparoscopic or robotic surgery. The Laparoscopic Visualization System is used to keep the lens defogged and clean from the opening of an operation through its close. Additionally it provides a true white balancing feature for better resolution. When the Laparoscopic Visualization System is activated and affixed to the patient's drape the Laparoscope is easily defogged and can be cleaned numerous times with the use of just one hand in as little as 5 seconds providing optimum visualization for surgery from opening to close. Most importantly the Laparoscopic Visualization System provides an innovation that helps provide improved patient care.

The Laparoscopic Visualization System works in the following manner. The compact unit is affixed to a patient's drape allowing quick access to the defogging/cleaning system using only one hand. In just 5 minutes, the anti-fogging solution warms to approximately 120.degree. F. to warm the endoscopic camera distal lens. The liquid quickly breaks down fats and tissue debris adhered to the lens. The Laparoscopic Visualization System is compatible with laparoscopes from 5 mm to 12 mm in diameter. The liquid is maintained warm for up to 6 hours. The Laparoscopic Visualization System can also provide true white balancing for better color visualization needed in Laparoscopic surgery. A microfiber pad included with the unit is used to remove tissue remnants without scratching or smudging the valuable laparoscope or robotic lenses. Two soft Micropad® towels can be provided in the form of a kit to help remove any persistent tissue remnants on the lens of the surgical device without leaving lint or smudging. The Micropad® towels are used to replace the use of coarse surgical gauzes which are harder on the lens. The Micropad® towels are also radio opaque helping to find them in the unlikely event they are ever left inside a patient. A TrocarWipe™ elongated cleaner is included in the kit to help clean the inside of the trocar/cannula. As mentioned earlier when not in use the laparoscope can be placed on standby inside the Laparoscopic Visualization System, maintaining cleanliness and protecting the lens. This positioning inside the Laparoscopic Visualization System prevents accidental burning of the patient caused by the high temperature created by the Laparoscope tip. The Laparoscopic Visualization System is the only system that keeps laparoscopes defogged and cleaned from start to close.

In another embodiment a cloth like material is placed inside the Top Valve Cover to absorb any liquid that may leak out of the Inner Assembly. This cloth like absorbent material can take a shape similar to the inside of the foam body.

An additional feature of the Laparoscopic Visualization System is its ability to absorb heat generated by the high intensity laparoscopic light source. When not in use, placing the laparoscope inside the heated can assembly reduces the possibility of small fires and patient burns caused by the high performance light source resting on the paper drapes or patient.

There is a need in the field for a reliable, efficient Laparoscopic Visualization System. The present invention overcomes the deficiencies of the known art and the problems that remain unsolved by providing a method and apparatus for efficiently heating and cleaning laparoscopic devices in a sterile environment.

These and other aspects, features and advantages of the present invention will become more readily apparent from the attached drawings and the detailed description of the preferred embodiments, which follow.

BRIEF DESCRIPTION OF DRAWINGS

The preferred embodiments of the invention will hereinafter be described in conjunction with the appended drawings provided to illustrate and not to limit the invention, in which:

FIG. 7A presents a Top view of the Laparoscopic Leakage Reducer.

FIG. 7B presents a Side Perspective view of the Laparoscopic Leakage Reducer.

FIG. 7C presents a Top view of the Laparoscopic Leakage Reducer.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration," Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise The Laparoscopic Visualization System or device 10 FIG. 1 comprises an outer shell 200 FIG. 2 made of a soft foam, rubber, or other shock absorbing material. Not only is the material of the shell shock absorbing, but it serves as a thermal insulator as well, helpful not only in maintaining the temperature of the structures therewithin but also keeping heat from escaping from within the shell. The shell 200 is designed to protect a distal lens of a laparoscope or other scope (not shown) from damage prior to, during, and after a surgical procedure.

Figure 1:
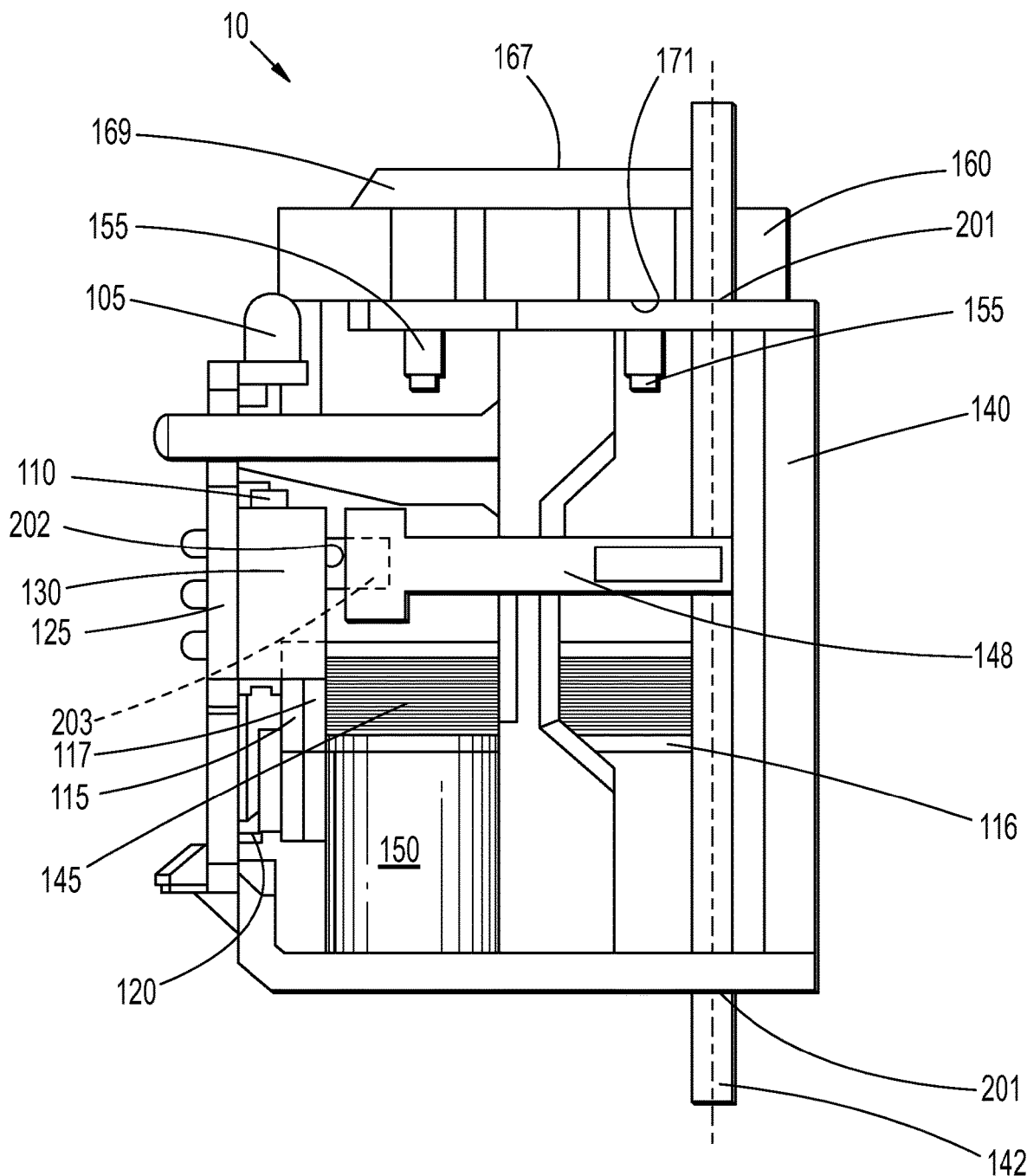
FIG. 1 presents an isometric view of the Inner Assembly of the Laparoscopic Visualization System.

Interior major components of the Laparoscopic Visualization System 10 are illustrated in their assembled manner in FIG. 1. The primary assembly is called the Inner Assembly. It encompasses all the major elements of the Laparoscopic Visualization System 10. An indicator 105 is always used for differentiating when the device is on or off. In the preferred embodiment the Laparoscopic Visualization System 10 uses a blue emitting LED 105, as the indicator. Blue is the preferred color because it is easily seen in the operating room. White is not the preferred LED color choice because it is not always readily visible. Among the many advantages of using an LED 105 as the main indicator, are its low cost, low and efficient power consumption, its resistance to vibration and shock damage, its low heat generation, its insensitivity to lower temperatures such as in an operating room, its ability to be unaffected by on/off cycling and its long life cycle. The LED 105 may also serve to warn when the batteries are becoming weak by flashing intermittently. In a further embodiment it is possible to have several LEDs 105 or one multifunctional LED 105, as the indicator 105. In a different embodiment (not shown) a small light bulb or temperature change color sticker can be used.

A printed circuit board (PCB) 125 is used for containing all operating circuitry for the assembly 10 and a resistor 110 is incorporated into the PCB 125 and has a resistance of between 10 and 1000 ohms. One of the purposes of the resistor 110 is to control the current passing through the LED 105, which in turn controls the brightness of the LED 105. Another factor affecting the brightness of the LED 105 is the length of Heating Coil 145. By extending the length of the Heating Coil 145, the resistance increases thus increasing the current going to the LED. The resistors 110 value must also be changed in order to maintain the same brightness to the LED 105. As the length of heating coil 145 is extended, power production drops. This is demonstrated by applying Ohms law E=I×R, where the voltage E remains constant in a parallel circuit. By increasing the length of the heating coil 145, the resistance increases, causing the branch current to decrease. This affects the brightness of the LED 105 in the adjacent parallel circuit. As the coil 145 resistance increases the current in the adjacent parallel circuit also increases causing the LED 105 to become brighter. A resistor in series with the LED helps to control the brightness. By applying the power formula P=V.sup.2/R, it is clearly demonstrated why less power is produced in this branch. In another embodiment, no resistor or LED is used.

Figure 3:
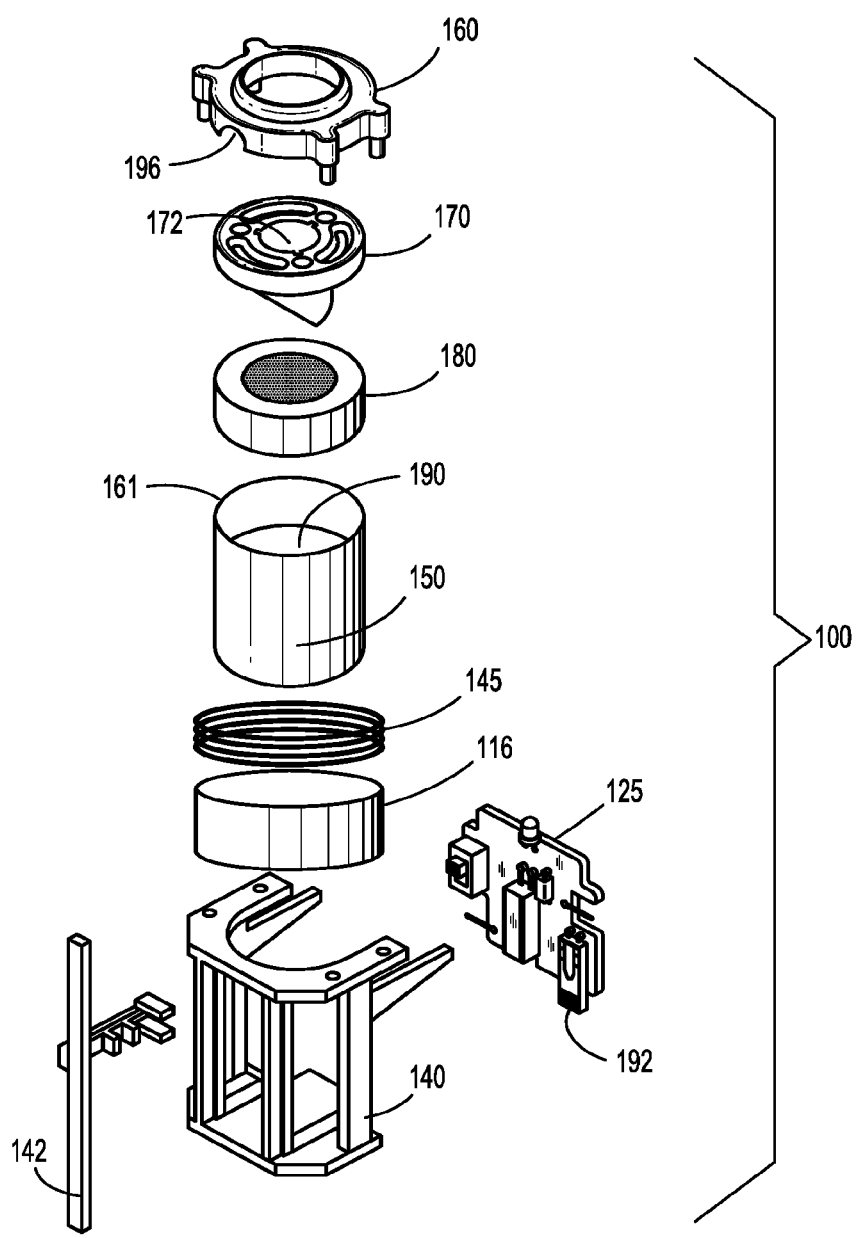
FIG. 3 presents an exploded Isometric view of the Laparoscopic Visualization System Inner Assembly.
Figure 12:
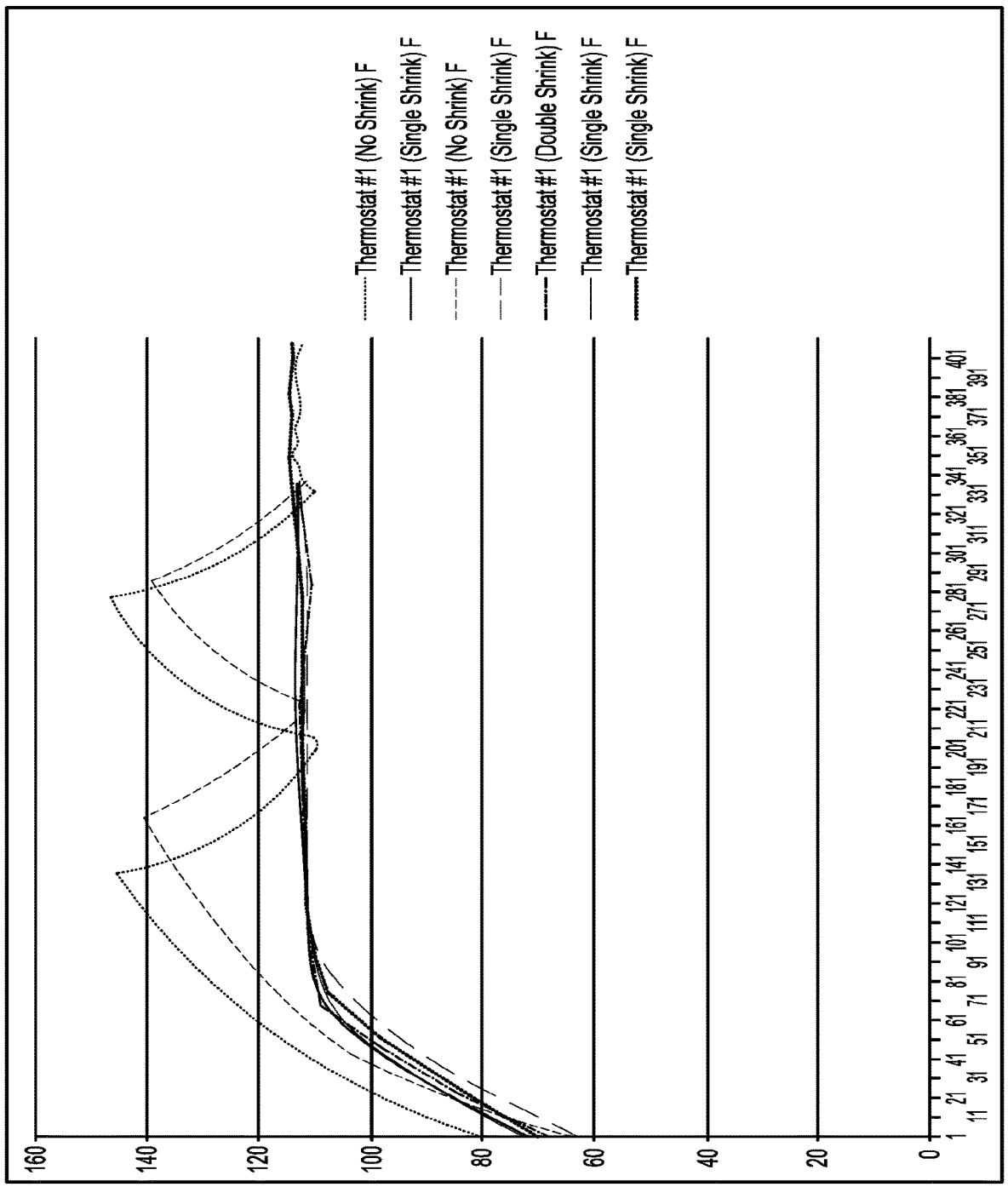
FIG. 12 presents a graph showing temperature variations with both insulated and uninsulated thermo switches of the System.

One of the major advances in the present Laparoscopic Visualization System 10 is the arrangement and location of a Thermoswitch 115. Through empirical testing and analysis, it has been determined that the most efficient and stable temperature control of the anti-fog solution is achieved when the Thermoswitch 115 is positioned as shown in FIG. 3 directly over the Heating Coil 145, and just below the level of the liquid (most preferably water containing a surfactant for convenience referred to as surfactant 190). The Laparoscopic Visualization System 10 is maintained between 50-70.degree. C. (122-158.degree. F.). Functionality determines the temperature range selected; Le, defogging, cleaning, etc. Outstanding results were ultimately obtained by providing a wrapping material 116 in the form of a pellicle that serves as a compression cuff for pressing the thermoswitch 115 into close physical and thermal transfer relationship with both the can assembly 150 and the heating element 145. The wrapping material 116 has four primary functions: It stabilizes the thermoswitch 115; element 145 and can assembly 150 against shock and vibration; it holds the thermoswitch 115 in heat transfer relationship with both the element 145 and the fluid in the can assembly 150; it acts as a thermal insulator by reducing heat loss; and finally it secures the thermal transfer switch 115, coil 145 and can assembly 150 together as a unit. In a preferred form, the wrapping material 116 is a pellicle of heat shrink plastic such as any suitable grade of thermoplastic heat shrink resin in the form of a circular band about 1¼ inches in diameter which after being slipped over the can assembly 150 and thermoswitch 115 is warmed with a heat gun until it shrinks sufficiently to tightly compress the thermoswitch 115 securely and in thermal transfer relationship with the coil and can assembly 150. We prefer to use a heat shrink pellicle that has a thickness of at least about 0.005 inch since it was found to also be effective as a thermal insulator in enhancing the temperature stability of the thermoswitch 115 while at the same time maintaining efficient heat transfer from the fluid and coil 145 to the thermoswitch thereby improving overall thermal efficiency of the complete system as described more fully in connection with FIG. 12 thereby substantially prolonging battery life. The ideal temperature range for the Laparoscopic Visualization System 10 will depend on several factors, among them are the length of heating coil 145, the location of the heating coil 145, and the amount of heat wrapping material 116 covering the Thermoswitch 115. When wrapping material 116 is used in accordance with the present invention, outstanding temperature stability is achieved, as demonstrated in the chart of FIG. 12. The two saw tooth lines show temperature variations where no insulation surrounds the Thermoswitch 115. In contrast the narrow edged lines indicate a stable better controlled temperature variation. Single or double insulation can be used for covering the Thermoswitch 115.

In the preferred embodiment, there is minimal insulation between the Thermoswitch 115, and Heating Can Assembly 150, resulting in better heat transference to the antifog solution inside the Heating Can Assembly 150 from the heating coil 145 coiled there around. In the preferred embodiment, Thermoswitch 115 is a mechanical type switch. The configuration of the Main Framework 140 may require the Thermoswitch 115 to be off center. The Main Framework 140 is specially designed, sized and configured to provide a means of securely attaching and holding all the components in the correct orientation. The Thermoswitch 115 may be in the form of a temperature sensor made of bi-metallic material or a thermocouple temperature sensing device in an IC or microcontroller. It may also be any heating resistive mechanism. In the preferred embodiment, a bimetallic strip type Thermoswitch 115 is used.

The bimetallic strip type Thermoswitch 115 is used to convert a temperature change into a mechanical displacement. The bimetallic strip type Thermoswitch 115 comprises two pieces of different metals which expand at different rates as they are heated. The bimetallic strip type Thermoswitch 115 can be made of steel and copper, or in some cases steel and brass, joined together throughout their lengths by riveting, brazing or welding. The different expansion rates force the flat strip to bend in one direction when heated, and in the opposite direction when cooled below the initial temperature. The metal with the higher coefficient of thermal expansion is usually placed on the outer side of a curve so that when the Thermoswitch 115 is heated, it displaces further.

Moving the heating coil 145, up or down the along a length of the heating can assembly 150 affects the ultimate temperature the antifog solution reaches. The Thermoswitch 115 is designed to open and close at pre-determined temperatures. If the Thermoswitch 115 is situated away from the heating coil 145 and the heating coil 145 is not positioned at or below the level of the antifog solution 190, more power will have to be generated by Power Source 205 of FIG. 2, to cause the Thermoswitch 115 to reach the desired cut off temperature. This explains why the orientation of the Thermoswitch 115 is so critical and why having it in the proper location significantly extends the useful life of the Laparoscopic Visualization System 10. The most important features of the Thermoswitch 115 are its quick temperature response time and self-resetting characteristics.

FIG. 1 also shows pin connectors 120 which connect the Heating Coil 145 to the PCB 125, completing the circuit. The improved simple connection allows quick assembly and significantly reduces the amount of human error during assembly. The Heating Coil 145 is preferably a 35 gauge copper enamel coated wire; copper being preferred. Nichrome can also be used, but in general any wire capable of conducting current, or any resistive heating element can also be used. The length of the heating coil 145 can be between 5-14 feet. In the preferred embodiment, the length is between 7-11 feet. This length provides the best balance and most efficient means to quickly reach the desired warming temperature. In order to provide the most efficient transfer of heat, the Heating Coil 145 needs to be tightly coiled in a single layer along the outside of Heated Can Assembly 150. By not using a multilayered winding, hot spots and shorting of the heating coil 145 are avoided. Each loop of coil 145 must be adjacent to and in contact with the next to generate an even, controlled amount of heat. The Heating Coil 145 is engaged through an On/Off switch 130 which is actuated through a lever 142 connected to an elongated side arm 148, actuated by a button 950 of FIG. 9B, on outer shell 200. The user just needs to depress the button 950 and the On/Off switch 130 will turn on the device 10, will turn on the LED indicator 105, and begin warming the Heating Coil 145. The main connection from Power Source 205 to the On/Off switch 130 is made through a connector 191, FIG. 2 on Printed Circuit Board 125 of FIG. 1. The lever 142, if necessary, may also be actuated by pushing upwardly thereon from below, within the shell 200 to turn the Laparoscopic Visualization System 10 off.

An improved Main Framework 140 of FIG. 3 is used to support the integrated parts comprising the Inner Assembly 100. The Inner Assembly 100 integrates the Printed Circuit Board 125, the Heating Can Assembly 150, and Beveled Valve Cap 160 and the lever 142 on the main framework 140, as well as for allowing positioning of the wrapping material to heating coil 145 within its confines.

Figure 2:
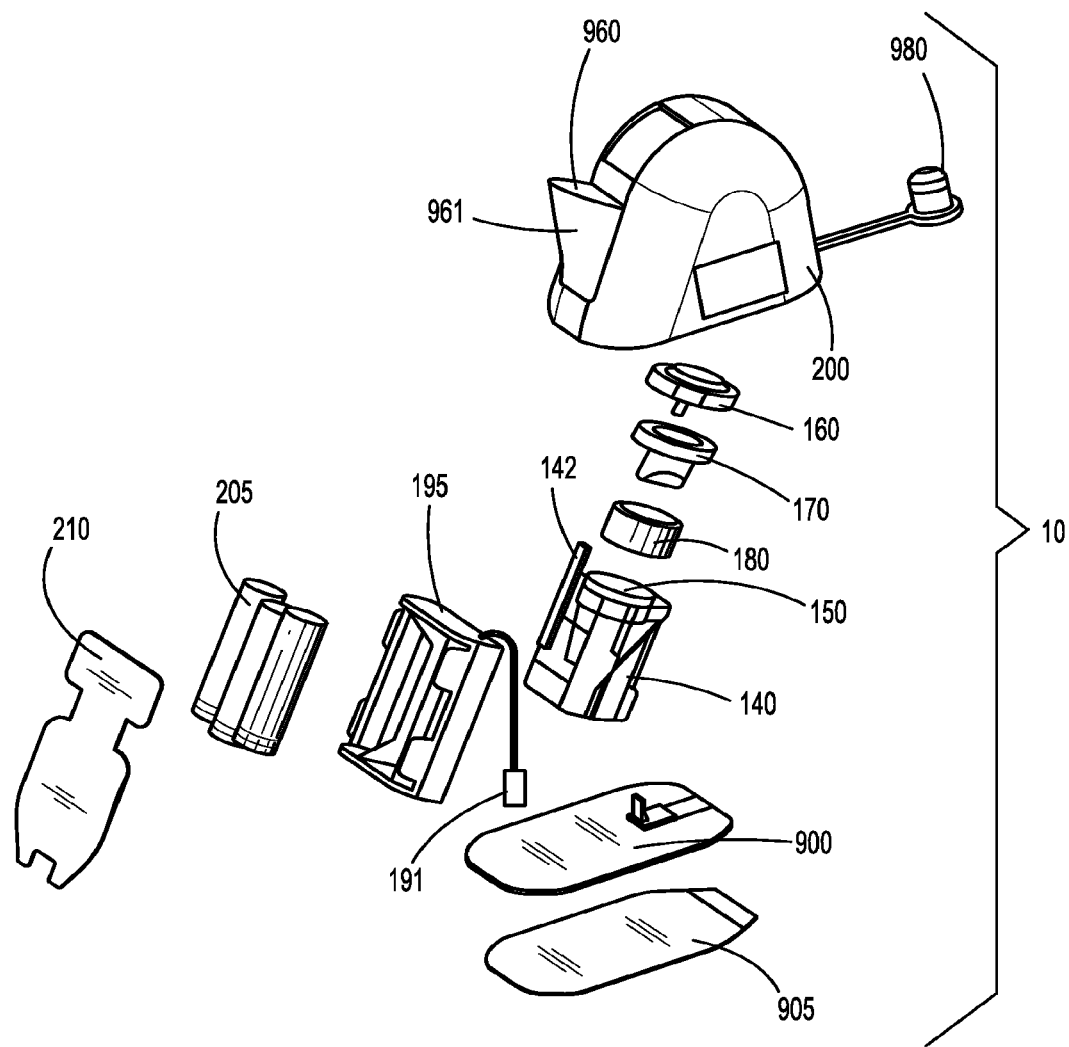
FIG. 2 presents an exploded Perspective view of the Laparoscopic Visualization System.

FIG. 2 provides an exploded view of the internal elements of the Laparoscopic Visualization System 10 within shell 200. The plastic or ceramic beveled Valve Cap 160 is used to lock the Insertion Valve 170 in place and can be held in place by gluing, applying wrapping material or any other industry standard method. A cup 180, made of a firm yet flexible material, such as a foam, for example, is seated within a base area of the heating can assembly 150 and is used to protect the distal lens of a Laparoscope from damage and scratching when inserted. An extra feature of the cup 180 is that it can also be used for white balancing. The cup 180 may also be made of rubber, cloth, sponge or felt materials.

Figure 9A:
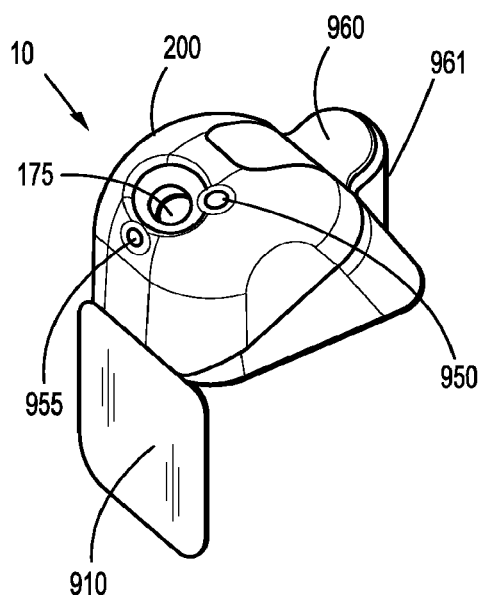
FIG. 9A presents a Side Perspective view of the Laparoscopic Visualization System Body Assembly.

The main framework 140 holds the key elements of the Laparoscopic Visualization System 10. When the On/Off Button 950 of FIG. 9A is depressed, lever 142 which mechanically engages and moves an elongated sidearm 148 in functional communication with the internal On/Off switch 130 turning it on, thus activating the Laparoscopic Visualization System 10. A Battery Holder 195 is used to hold three AA batteries 205, forming power source 205, in place. Battery Holder 195 provides power to the Assembly 10, through power connector 191. An optional battery Pull Tab 210 of FIG. 2 is used to provide a means of extracting the batteries. The Laparoscopic Visualization System shell 200 is covered along the bottom with a Bottom Cover Assembly 900. The Laparoscopic Visualization System Bottom Cover assembly 900 has the option of having an adhesive Strip 905 to secure the Laparoscopic Visualization System shell 200, to the patient or an anchoring site. The Laparoscopic Visualization System shell 200 engages an external Laparoscopic Reducer 980 FIG. 2. This reducer can also be custom sized to fit custom made laparoscopes.

The framework 140 includes top and bottom slots 201 of FIG. 1, which engage around the lever 142 in a manner where it is slideable between an up (off) position and a down (on) position, relative to an actuator 202 of the on/off switch 130 which engages within a slot 203 formed in side arm 148 of the lever 142.

In the preferred embodiment the Laparoscopic Visualization System 10 of FIG. 2 uses surfactant 190 in the form of a sterile fluid 190, however sterile water, sterile saline, or any sterile anti-fog solution may also be used. In the preferred embodiment, 5 ml of liquid 190 is reserved in the canister 150. Evaporation of the liquid 190 in the canister 150 is not a concern because of the enclosed environment within canister 150. Another important consideration is that the surfactant 190, with respect to the orientation of the heating coil 145, must be such that heat can transfer effectively, including when the canister 150 is in a horizontal position. It will be understood that the duckbill valve 174 in inset, along a top level of the liquid 190 so that, when placed on its side, the main volume of the liquid remains within a small area beneath the duckbill valve 174 and in contact with the heating coil 145 to maintain the temperature thereof as constant as possible.

FIG. 3 illustrates a detailed internal view of key elements of Inner Assembly 100. The beveled Valve Cap 160 holds the Laparoscopic Insertion Valve 170 in place over the entrance to the Heated Can Assembly 150, with the Printed Circuit Board 125 the Heating Coil 145 being mounted to the Main Framework 140 as well, forming the inner assembly 100.

The Inner Assembly 100 of FIG. 3 includes beveled Valve Cap 160 which is held in place by at least two Valve Cap Elongated Prongs 155. The Prongs 155 are slightly offset, allowing the beveled Valve Cap 160 to securely lock into place over an entrance to heating can assembly 150 formed by a flexible insertion Valve 170, which is used to guide a laparoscope into heating can assembly 150. At least one Insertion Valve Expansion Orifice 172 is provided along an inner periphery of the insertion valve 170 to compensate for the different diameters of Laparoscopes used. The at least one insertion Valve Expansion Orifice 172 also permits air to escape from the Heated Can Assembly 150 upon insertion of a laparoscope.

The Heating Can Assembly 150 in its preferred embodiment is made of stainless steel. It is constructed of a biocompatible material and is inexpensive to produce. In other embodiments it can be made of Plastic, Aluminum, Ceramic or a combination thereof or of other metals that have excellent heat conductivity. The thickness of the Heated Can Assembly 150 is an important consideration because it determines the heating properties. The thickness of the Heated Can Assembly 150 can be between 0.1 to 0.75 mm. In FIG. 3 top 161 of the Heating Can Assembly 150 is slightly flared allowing the beveled Valve Cap 160 to have a tighter and better fit when secured thereon.

The Insertion Valve 170 includes several important qualities. Among them are its construction, being made of a flexible rubber or plastic material that permits instruments whose diameters are between 2-12 mm to be inserted snugly, thus permitting only minimal leakage. The Laparoscopic Insertion Valve 170 must be designed to allow easy passage of other medical devices, and it is self-sealing once the medical devices are removed. In the preferred embodiment the Laparoscopic Insertion Valve 170 helps to control pressure in the heating can assembly 150, which can be accomplished by any suitable means, such as by the provision of a compressible bladder 500 of FIG. 6B, or a one way venting or duckbill valve 174.

Figure 4:
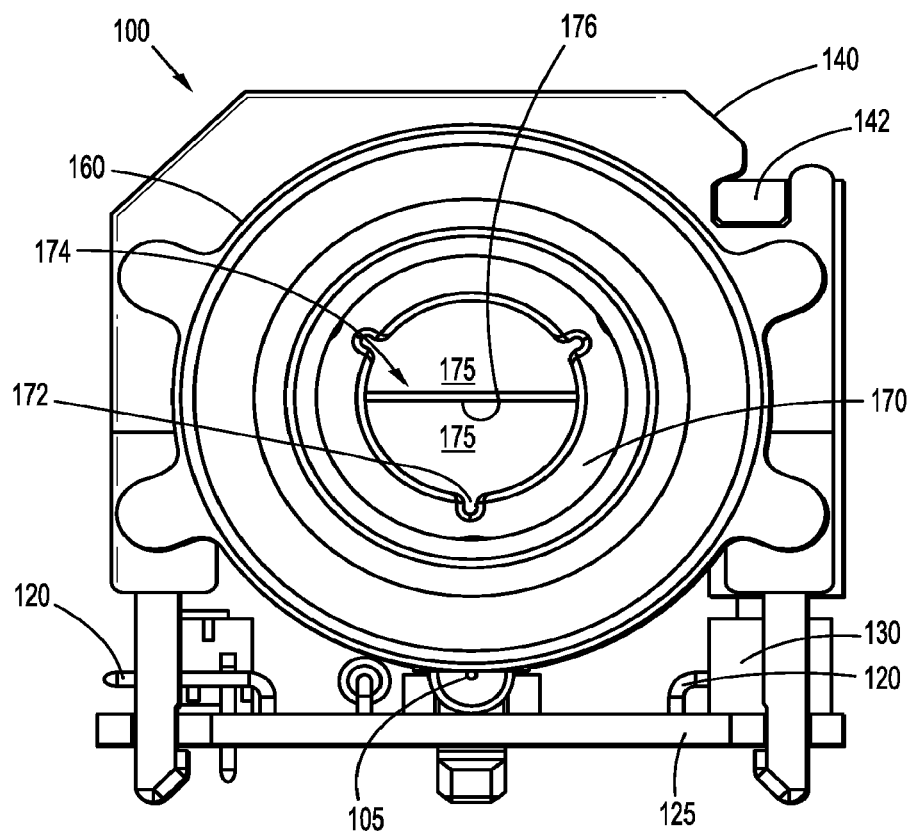
FIG. 4 presents a top view of the Laparoscopic Visualization System Inner Assembly.

FIG. 4 illustrates a top view of Inner Assembly 100. The beveled Valve Cap 160 has at least one cut away recess 196 that is better seen in FIG. 3. Recess 196 permits the LED 105 to fit closely to the Valve Cap 160. The cut away recess 196 also reduces the overall size of the Inner Assembly 100. How the PCB 125 mechanically engages the Main Framework 140 is also illustrated. FIG. 4 shows the symmetry and ergonometry of the beveled Valve Cap 160 with respect to the Main Framework 140. Insertion Valve 170 further includes a normally closed duckbill or one way venting valve 174 comprising two mating flexible sections 175, the mating edges 176 of which is closed when nothing is inserted into the heating can 150, the duckbill valve 174 being spaced downwardly from the beveled cap 160, at a position just above the level which liquid 190 reaches, the duckbill valve 174 being in a normally closed position.

Figure 5:
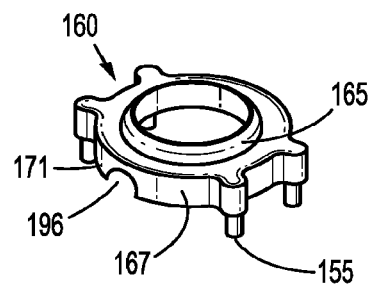
FIG. 5 presents a Perspective view of the Top Cap Assembly.

FIG. 5 Illustrates a Perspective view of the beveled Cap Assembly 160. A smooth Beveled Valve Cap Opening 165 is used to help guide the laparoscope into the Heated Can Assembly 150. A side wall 167 of the Valve Cap 160 is designed so that its height is sufficient to provide a secure fit over the Insertion Valve 170 of FIG. 6B. There are at least two Valve Cap Elongated Prongs 155 symmetrically located on the bottom 171 of the Valve Cap 160 which are used for securing the Valve Cap 160 to the Main framework 140 over the entrance to Heating Can Assembly 150.

Figure 6A:
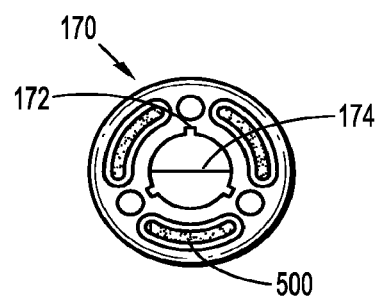
FIG. 6A presents a Top view of the Laparoscopic Insertion Valve.
Figure 6B:
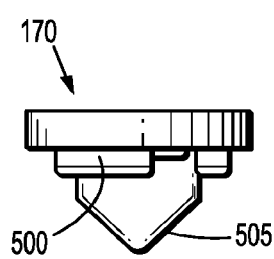
FIG. 6B presents a Side Isometric view of the Laparoscopic Insertion Valve.
Figure 6C:
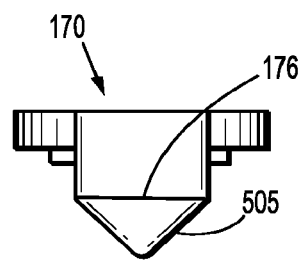
FIG. 6C presents a Cross Sectional view through the Laparoscopic insertion Valve.

FIG. 6A illustrates a Top View of the Laparoscopic Insertion Valve 170. The Insertion Valve 170 and duckbill valve 174 provide a point of entry for the insertion device. A special Insertion Valve Expansion Bladder 500 of FIG. 6B is provided to compensate for the pressure displacements caused by the insertion of laparoscopic devices into the canister 150 and to compensate for the expansion that takes place when the liquid 190 is heated. The compressible valve expansion bladder 500 provides a mechanism for pressure control within canister 150.

FIG. 6B illustrates a Side View of the Laparoscopic Insertion Valve 170, with expansion bladder 500 protruding. The expansion bladder 500 serves a further purpose, for the insertion of a leakage Reducer 700. The leakage Reducer 700 is a major improvement to the Laparoscopic Visualization System 10. It assists in preventing leakage of liquid that may have escaped from the Insertion Valve Duck Bill 174 of FIG. 6B that expands to allow a Laparoscopic device to enter and provides a tight fit there around, inside the Heated Can Assembly 150.

FIG. 7A, illustrates a top Isometric View of the Laparoscopic Leakage Reducer 700. The Leakage Reducer 700 provides an opening for the Insertion Valve Expansion Bladder 500 of FIG. 6B to securely engage within the canister 150. The Leakage Reducer 700 locks into place with the Laparoscopic Insertion Valve 170 of FIG. 6A, providing a secondary leakage preventing structure and a tool used for accommodating different sized medical devices. The leakage Reducer 700 can be permanently attached as one piece or as two separate pieces.

Figure 9B:
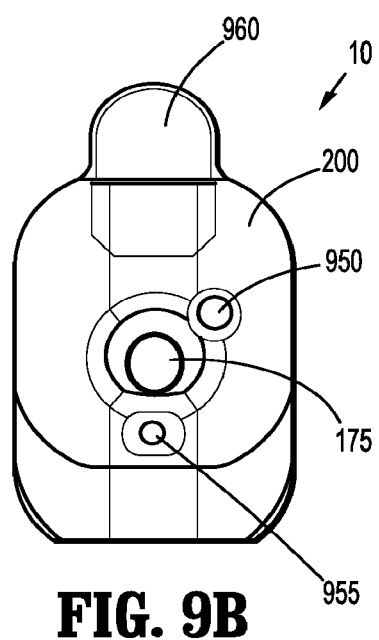
FIG. 9B presents a Top Perspective view of the Laparoscopic Visualization System Body Assembly.
Figure 9C:
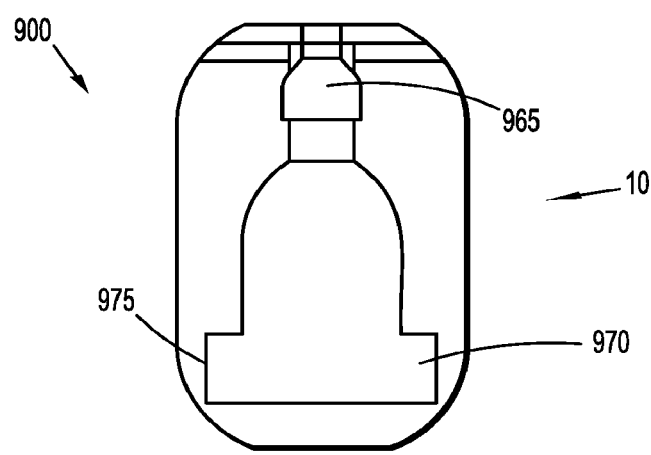
FIG. 9C, presents a Bottom Isometric view of the Laparoscopic Visualization System Body Assembly.

In the preferred embodiment the attached tethered Reducer 980 of FIG. 2 connects at Recessed Reducer Attachment Area 965 of FIG. 9C. It is snapped into place through the recessed opening 175 of FIG. 9A, providing a firm snug fit for Laparoscopic devices. This further minimizes the leakage potential for the surfactant 190.

FIG. 7C illustrates a U-shaped projection on the inner surface of retainer 700 that at least partially surrounds aperture 705 to serve as a spacer 710 to keep a pressure release aperture in the leakage reducer 700 from being obstructed, e.t. by a part of valve 170 when the surgical scope is inserted into the chamber. The U-shaped spacer 710 provides a unique means for enabling air to escape with little or no loss of the surfactant liquid 190.

Figure 8A:
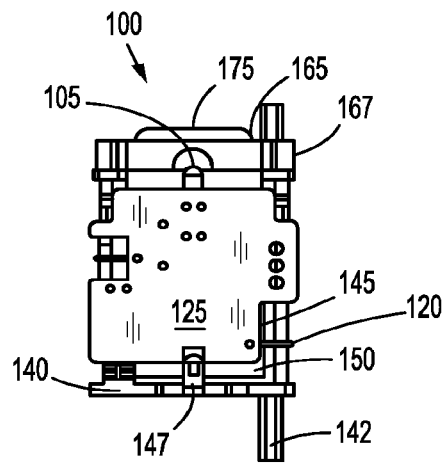
FIG. 8A presents a Backside Isometric view of the Laparoscopic Visualization System Inner Assembly.

FIG. 8A shows the orientation of the PCB 125 and the inner assembly 100 of Laparoscopic Visualization System 10. A small gap defines the outer chamber within the Main Framework 140, and the Heating can assembly 150, allowing the heating coil 154 to be received within the main framework 140.

Figure 8B:
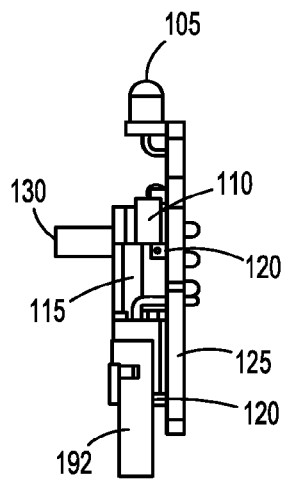
FIG. 8B presents a Side view of the Laparoscopic Visualization System PCB.
Figure 8C:
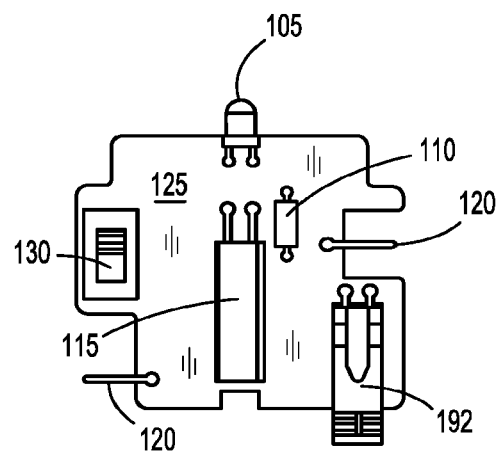
FIG. 8C presents a Front view of the Laparoscopic Visualization System PCB showing its components.

FIGS. 8B and 8C show the compactly designed simple PCB 125, incorporating the On/Off switch 130, the LED 105, the Resistor 110, illustrating the location and orientation of the Thermoswitch 115, and the Heating Coil connector pins 120 as well. This ergonomic design dramatically reduces the potential for human error during assembly. The integration of the above defined structures into the PCB 125 significantly improves quality control, manufacturing and assembly of the Laparoscopic Visualization System 10. A PCB battery connector 192 is provided for quickly connecting the battery pack 195 connector 191. A PCB locking feature 147 of FIG. 8A is also employed to help secure the PCB 125 to the main framework 140.

FIG. 9A illustrates a side view of the shell 200 of the Laparoscopic Visualization System 10. Recessed opening 175 shown allows and helps guide a Laparoscope into the Heating Can Assembly 150. A bottom cover 910 of Bottom Cover assembly 900 can be used for securely attaching the Laparoscopic Visualization System 10 to a suitable structure within the surgical field during laparoscopic procedures. An endoscopic Lens Cleaning Pad 960 attached via a rear flange 961 is used to clean the Laparoscopic lens before or after insertion into the Heated Can Assembly 150. The circular opening 955 is formed as part of the housing assembly. The blue LED 105 indicator projects light through a circular opening 955 in the shell 200.

FIG. 9B illustrates a Perspective view of the shell 200 of the Laparoscopic Visualization System 10. The figure demonstrates how user friendly the Laparoscopic Visualization System 10 is to the surgical team with its simple design, letting the user know when it is activated, by illumination means and warming the liquid 190 used for cleaning the lens.

FIG. 9C illustrates an Isometric view of the bottom cover assembly 900 of Laparoscopic Visualization System 10. An optional additional Recessed Reducer attachment area 965 may be incorporated to compensate for attaching different sizes of valve reducer 980. A Bottom Housing Assembly Opening 970 is configured to easily allow the inner assembly 100 of the Laparoscopic Visualization System 10 to be inserted into the shell 200 through the bottom. Battery Holder Insertion Opening 975 is specially cut out to allow Battery Holder 195 to snugly and frictionally fit into the shell 200, and glue or other adhesives can be applied to further secure the inner assembly 100 in the shell 200.

Figure 10:
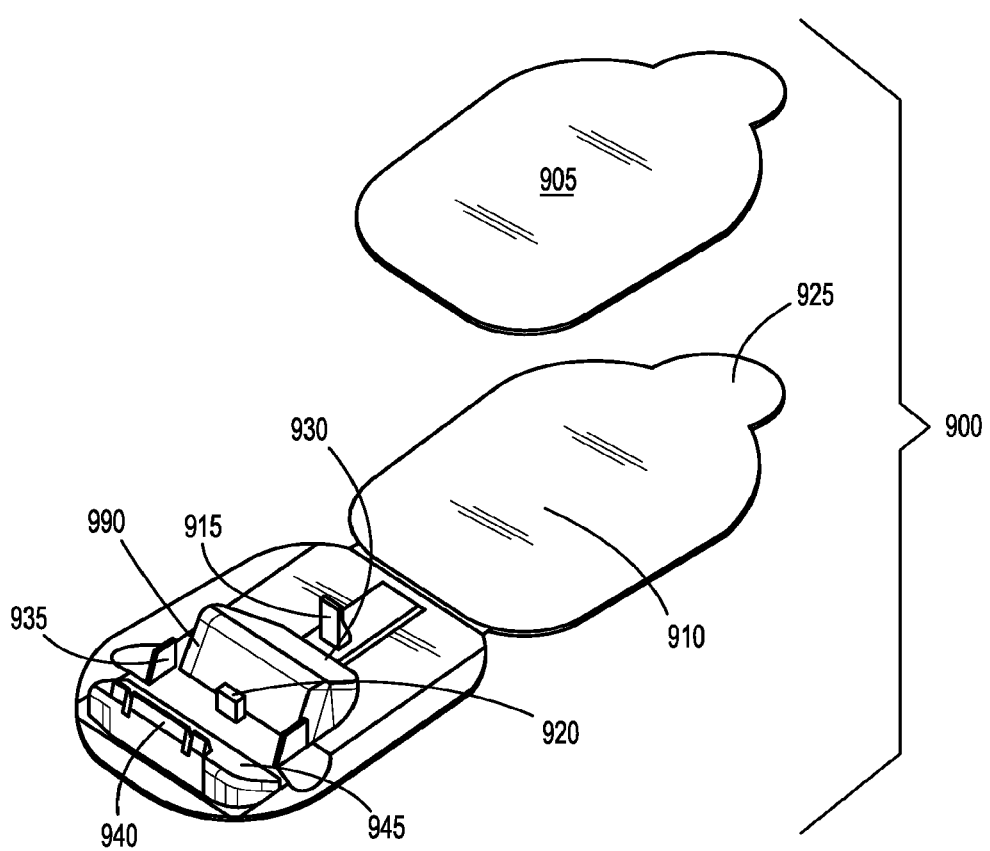
FIG. 10 presents a Perspective view of the Bottom Cover Assembly.

FIG. 10 illustrates a Perspective view of the Bottom Cover Assembly 900. A Bottom Cover adhesive 905 can be used to attach to Bottom Cover 910 to the body assembly 200. Its purpose is to provide means for securely attaching the Laparoscopic Visualization System 10 to a stationary object, preferably within the surgical field. A Bottom Cover Locking Insert 920 is also provided for attaching the Bottom Cover Assembly 900 to the shell 200. A special Housing Attachment Tab 915 is designed to clip onto or grab onto a bottom surface of the heating can assembly 150. A specially designed Clamping Tab 925 is also provided for attaching the Laparoscopic Visualization System 10 to a secure object during surgery. A Bottom Support Member 930 is designed at an angle and is used for holding the Inner Assembly 100 in place. A Bottom Battery Locking Latch 940 is used to provide an attachment for the Bottom Cover assembly 900. A Bottom Battery Angled Support 945 is used to secure Battery holder 195 inside the shell 200.

In a further proposed embodiment, the Laparoscopic Visualization System 10 may incorporate brushes or other mechanical means for cleaning various Laparoscopic instruments. The warmed liquid 190 in the Heated Can Assembly 150 may also be used to warm and clean other types of Laparoscopic Instruments, thus acting as a multipurpose instrument cleaner.

Figure 11:
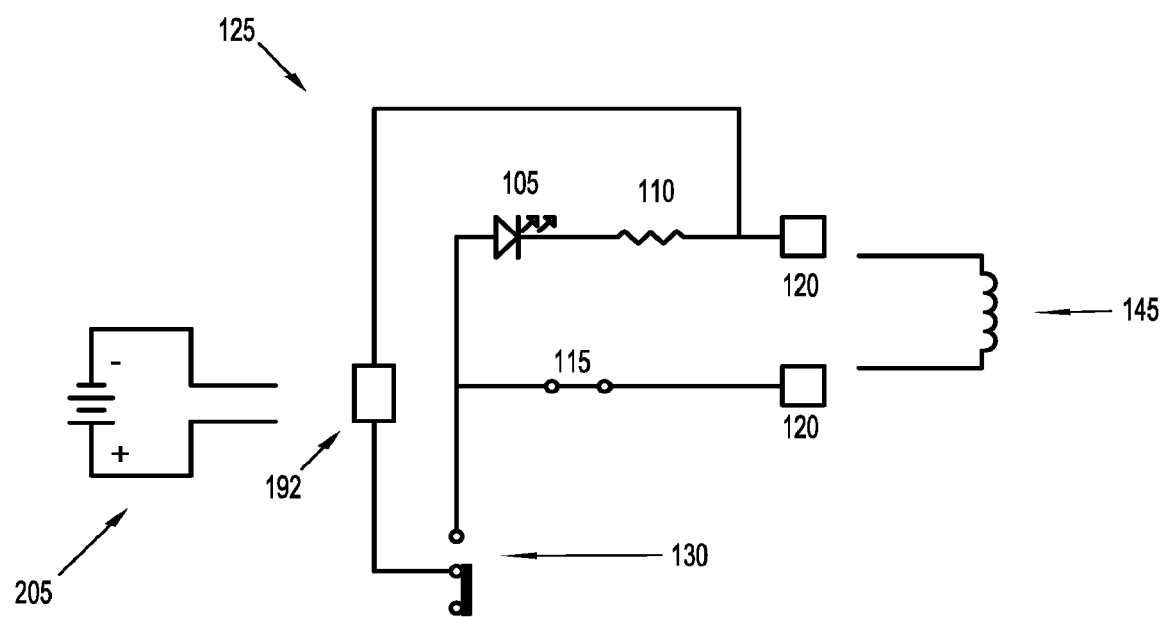
FIG. 11 presents an Electrical schematic of the preferred embodiment.

FIG. 11 presents an electrical schematic of the preferred embodiment wherein all the essential elements are shown. A power supply 205 consisting of three (3) AA batteries 205 is the source that drives the circuitry. An on/off switch 130 in the normally open position is connected in series with the simple parallel circuit presented on the PCB 125 that provides heating and "On" indication to the Laparoscopic Visualization System 10. Further, normally closed Thermal Switch 115 connects in series with the Heating Coil assembly 145. The Heating Coil 145 is connected to heating coil pin connectors 120 at points as illustrated. When the temperature of the Heating Can Assembly 150 reaches a predetermined temperature, it causes the Thermoswitch 115 to open, breaking the electrical current going into the heating coil assembly 145. Whenever the temperature within heating can assembly 150 drops below a predefined lower temperature threshold, the Thermoswitch 15 closes and allows current to flow into the Heating Coil 145 to warm liquid 190. Although in the preferred embodiment the power source 205 is a DC source it does not preclude use of an AC power source.

In a further embodiment thermal epoxy 117 of FIG. 1, may be used for better transference of heat from the heating coil 145 to the thermal switch 115. One advantage of using thermal epoxy 117 is that it allows the bi-metallic Thermoswitch 115 to freely expand and contract without any physical restriction or hindrance.

As will be recognized by those of ordinary skill in the pertinent art, numerous modifications and substitutions can be made to the above-described embodiments of the present invention without departing from the scope of the invention. Accordingly, the preceding portion of this specification is to be taken in an illustrative, as opposed to a limiting sense.

What is claimed is:

1. A laparoscopic visualization system comprising:
  a housing comprised of an insulating, substantially rigid material, the housing having a central chamber, an outer surface of the housing including an inlet including a normally closed valve therein, the inlet communicating with the central chamber to allow a distal end of a surgical scope to be inserted into the central chamber through the inlet, the valve sealing around the distal end of the surgical scope when inserted and the valve closing off the central chamber upon removal of the surgical scope distal end therefrom;
  the central chamber being configured to allow a distal end of a surgical scope to be received therein when inserted through the inlet and to be submerged in and heated by a warmed anti-fogging liquid solution within the central chamber;
  a heating coil coiled around the central chamber for heating an anti-fogging liquid solution contained within the central chamber in a narrow range, controlled manner to clean and warm a distal lens of the surgical scope submerged in the heated anti-fogging solution; and
  electrical circuitry including a thermoswitch for controlling the temperature of the liquid solution within the central chamber,
  wherein the heating coil is positioned between the central chamber and a layer of wrapping material within the housing that presses against the outer surface of the thermoswitch for urging the thermoswitch toward the central chamber.

2. The laparoscopic visualization system of claim 1 wherein the heating coil is positioned below the level of liquid solution within the central chamber.

3. The laparoscopic visualization system of claim 1 wherein the laparoscopic visualization system is disposable.

4. The laparoscopic visualization system of claim 1 further comprising:
  an on/off switch provided for controlling activation of the electrical circuitry; and
  means for indicating the on condition of the system.

5. The laparoscopic visualization system of claim 1 wherein the wrapping material is a circular pellicle surrounding the central chamber.

6. The laparoscopic visualization system of claim 1 wherein the thermoswitch is positioned over the heating coil.

7. The laparoscopic visualization system of claim 1 wherein the thermoswitch is in heat-conductive relationship with the central chamber.

8. The laparoscopic visualization system of claim 1 wherein the thermoswitch is configured to control the temperature of the liquid solution within the central heating container within a predefined, narrow range of temperatures so as to maintain the temperature of the liquid solution substantially constant.

9. The laparoscopic visualization system of claim 1 wherein the wrapping material is configured to press the thermoswitch into close physical and thermal transfer relationship with the central chamber.

10. The laparoscopic visualization system of claim 1 further comprising means for reducing pressure within the central chamber when a distal end of the surgical scope is inserted into the central chamber to keep liquid solution from being forced out of the central chamber.

11. The laparoscopic visualization system of claim 1 wherein a thermal epoxy is inserted between the heating coil and the thermoswitch.

12. The laparoscopic visualization system of claim 1 wherein the valve prevents the anti-fogging liquid solution from spilling out of the central chamber when the distal end of the surgical scope is removed therefrom.

13. The laparoscopic visualization system of claim 1 wherein a duckbill valve is positioned at a level just above the level the liquid solution reaches in the central chamber.

14. A laparoscopic visualization system comprising,
  a shell to serve as an enclosure, the shell having a chamber for holding a liquid into which a surgical scope can be inserted,
  a heating element in thermal transfer relationship with the chamber for warming the liquid therein,
  wherein the chamber comprises a vessel having a wall surrounding a central compartment adapted to contain the liquid with the heating element in thermal transfer relationship therewith,
  a thermoswitch in heat-conductive relationship with the vessel,
  a wrapping material as a compression element for pressing the thermoswitch into close physical and thermal transfer relationship with the vessel, and
  means for reducing pressure within the chamber when a distal end of the surgical scope is inserted into the chamber to keep liquid solution from being forced out of the chamber while a proximal end of the surgical scope is outside of the shell,
  wherein the wrapping material surrounds the vessel and presses against the outer surface of the thermoswitch for urging the thermoswitch toward the vessel, and wherein the wrapping material is a thermoplastic resinous film that is shrunk onto the thermoswitch and the vessel by the application of heat thereto.

15. The laparoscopic visualization system of claim 14 wherein the wrapping material is a circular pellicle surrounding the vessel that presses against the outer surface of the thermoswitch for urging the thermoswitch toward the vessel.

16. The laparoscopic visualization system of claim 15 wherein the thermoswitch includes a thermal sensor element for opening an electrical circuit to an electrical power source when the thermoswitch reaches a selected temperature, and wherein the pellicle is a ring of thermoplastic resinous film that is shrunk onto the thermoswitch and the vessel by the application of heat thereto.

17. The laparoscopic visualization system of claim 14 including a printed circuit board connected to the vessel, the printed circuit board having circuit components selected from the group consisting of a resistor, an indicator light and an on/off switch and such components being conductively connected together by printed circuit wiring applied to the circuit board.

18. The laparoscopic visualization system of claim 14 wherein the heating element is a heating coil which is positioned between the central compartment and a layer of the wrapping material within the housing.

19. The laparoscopic visualization system of claim 14 wherein the heating element is positioned below the level of liquid solution within the chamber.

20. The laparoscopic visualization system of claim 14 wherein the means for reducing pressure within the chamber comprises a compressible bladder.

* * * * *